US012121318B2

(12) United States Patent
Mercier et al.

(10) Patent No.: US 12,121,318 B2
(45) Date of Patent: Oct. 22, 2024

(54) LOW POWER MAGNETIC FIELD BODY AREA NETWORK WITH QUENCHING AND QUICK START

(71) Applicant: The Regents of the University of California, Oakland, CA (US)

(72) Inventors: Patrick Mercier, San Diego, CA (US); Jiwoong Park, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 652 days.

(21) Appl. No.: 17/429,495

(22) PCT Filed: Feb. 14, 2020

(86) PCT No.: PCT/US2020/018278
§ 371 (c)(1),
(2) Date: Aug. 9, 2021

(87) PCT Pub. No.: WO2020/168183
PCT Pub. Date: Aug. 20, 2020

(65) Prior Publication Data
US 2022/0095920 A1    Mar. 31, 2022

Related U.S. Application Data

(60) Provisional application No. 62/806,294, filed on Feb. 15, 2019.

(51) Int. Cl.
*A61B 5/00* (2006.01)
*H04B 13/00* (2006.01)

(52) U.S. Cl.
CPC .......... *A61B 5/0024* (2013.01); *A61B 5/0028* (2013.01); *A61B 5/6802* (2013.01); *H04B 13/005* (2013.01)

(58) Field of Classification Search
CPC ... A61B 5/0024; A61B 5/0028; A61B 5/6802; H04B 13/005
(Continued)

(56) References Cited

U.S. PATENT DOCUMENTS 4,980,898 A * 12/1990 Silvian ................. H03B 5/1221
331/165
5,999,857 A * 12/1999 Weijand ............... A61N 1/3727
128/903

(Continued)

FOREIGN PATENT DOCUMENTS

| CN | 102163982 A * | 8/2011 | |
| EP | 3648363 B1 * | 8/2021 | ............... H03L 7/08 |
| WO | WO-2017035143 A1 * | 3/2017 | ........... H04B 13/005 |

OTHER PUBLICATIONS

International Search Report and Written Opinion from the corresponding International Patent Application No. PCT/US2020/018278, dated Apr. 7, 2020.
(Continued)

*Primary Examiner* — Mong-Thuy T Tran
(74) *Attorney, Agent, or Firm* — Greer, Burns & Crain, Ltd.; Steven P. Fallon

(57) ABSTRACT

A transmitter for a magnetic body area network includes a power oscillator that directly uses a body coil as a resonant element. Shunt transistor circuitry is between the power oscillator and the body coil, the shunt transistor circuitry selectively shunts current from the body coil in response to a data signal provided to the transmitter. Power injection circuitry is synchronized to the power oscillator to selectively inject power into the body coil in response to the data signal. A tuning capacitor array is disposed to tune frequency in the body coil. A frequency-locked-loop responds to a frequency in the body coil and tunes the tuning capacitor array to lock to a carrier frequency. Very high Q coils can be
(Continued)

used while achieving high data transmission rates of 5 mbps to 10 mbps. Transmitters and methods are applicable to on-off-key modulation, frequency-shift modulation and amplitude-shift modulation.

18 Claims, 6 Drawing Sheets

(58) Field of Classification Search
USPC .......................................................... 455/41.1
See application file for complete search history.

(56) References Cited

U.S. PATENT DOCUMENTS

| | | | |
|---|---|---|---|
| 8,771,184 B2 | 7/2014 | Besson et al. | |
| 9,024,696 B2 * | 5/2015 | Li | H03D 3/22 |
| | | | 331/117 R |
| 9,831,847 B2 * | 11/2017 | Babaie | H03H 7/40 |
| 10,849,503 B2 * | 12/2020 | Melodia | A61B 5/0026 |
| 2014/0051965 A1 | 2/2014 | Zdeblick et al. | |
| 2015/0365115 A1 * | 12/2015 | Arne | H04B 1/1027 |
| | | | 375/284 |
| 2018/0241483 A1 | 8/2018 | Park et al. | |
| 2020/0064920 A1 * | 2/2020 | Soltani | G01S 13/0209 |
| 2021/0076937 A1 * | 3/2021 | Melodia | G16H 40/63 |

OTHER PUBLICATIONS

Hall et al., "Antennas and Propagation for On-Body Communication Systems", IEEE Antennas and Propagation Magazine, 2007, pp. 41-58, vol. 49, No. 3, IEEE.

Jang et al., "4-Camera VGA-Resolution Capsule Endoscope with 80Mb/s Body-Channel Communication Transceiver and Sub-cm Range Capsule Localization", 2018 IEEE International Solid-State Circuits Conference, 2018, pp. 282-284, IEEE.

Mercier et al., "A Sub-nW 2.4 GHz Transmitter for Low Data-Rate Sensing Applications", IEEE Journal of Solid-State Circuits, 2014, pp. 1463-1474, vol. 49, No. 7, IEEE.

Maity et al., "BodyWire: A 6.3-pJ/b 30-Mb/s—30-dB SIR-Tolerant Broadband Interference-Robust Human Body Communication Transceiver Using Time Domain Interference Rejection", IEEE Journal of Solid-State Circuits, 2019, bp. 2892-2906, vol. 54, No. 10, IEEE.

Park et al., "Channel Modeling of Miniaturized Battery-Powered Capacitive Human Body Communication Systems", IEEE Transactions on Biomedical Engineering, 2017, pp. 452-462, vol. 64, No. 2, IEEE.

Park et al., "Magnetic Human Body Communication", Annual International Conference of the IEEE Engineering in Medicine and Biology Society (EMBC), 2015, pp. 1841-1844, IEEE.

* cited by examiner

LOW POWER MAGNETIC FIELD BODY AREA NETWORK WITH QUENCHING AND QUICK START

PRIORITY CLAIM AND REFERENCE TO RELATED APPLICATION

The application claims priority under 35 U.S.C. § 119 and all applicable statutes and treaties from prior provisional application Ser. No. 62/806,294, which was filed Feb. 15, 2019.

FIELD

Example fields of the invention include network communications and body monitoring systems. Example body monitoring systems include body worn health sensing systems, activity trackers and body worn sports performance systems. Networks of the invention can provide communications for any wearable device that needs to wireless communicate information around the body (e.g., wearable sensors, activity trackers, smartwatches, headphones, microphones, smart glasses, medical monitors, exercise monitors, EEG headsets, etc.) with ultra-low-power consumption.

BACKGROUND

Prior Mercier et al., US 2018/0241483 provides solutions to the inherent energy consumption problems of far-field RF, which has significant path loss around the human body (e.g., up to 70 dB at 2.4 GHz), most RF body-area-network (BAN) systems such as Bluetooth Low Energy (BLE) have significant energy-expensive amplification requirements consuming milliwatts of power, and thus do not meet the energy demands of emerging small devices. Popular wireless earbuds, for example, only achieve a battery life of a few hours. Exasperatingly, emerging high-fidelity streaming audio and video content requires higher data rates than what BLE can currently accommodate.

Human body communication (HBC) systems, for example ones based on electric fields (eHBC), in theory have lower path loss and can thus potentially offer more efficient links [1-2]. However, measurements from form-factor-accurate prototypes reveal path loss that is still rather large (e.g., 45 dB across 20 cm [3]), with unfortunately severe variation with posture and environments that requires energy-expensive compensation. Since the human body is magnetically inert, magnetic HBC (mHBC) systems, offer much lower path loss (e.g., 5-30 dB [4]) without severe variation, and can thus theoretically achieve lower communication energy. Known mHBC systems still provide low bandwidth, especially when transmitter coil quality is increased to reduce path loss.

REFERENCES

[1] S. Maity et al., "A 6.3 pJ/b 30 Mbps −30 dB SIR-tolerant Broadband Interference-Robust Human Body Communication Transceiver using Time Domain Signal-Interference Separation," IEEE CICC, pp. 1-4, Apr. 2018.

[2] J. Jang et al., "4-Camera VGA-resolution capsule endoscope with 80 Mb/s body-channel communication transceiver and Sub-cm range capsule localization," ISSCC Dig. Tech. Papers, pp. 282-283, Feb. 2018.

[3] J. Park et al., "Channel Modeling of Miniaturized Battery-Powered Capacitive Human Body Communication Systems," IEEE. Trans. Biomed. Eng., pp. 452-462, Feb. 2017.

[4] J. Park et al., "Magnetic Human Body Communication," IEEE EMBC, pp. 1841-1844, Aug. 2015.

SUMMARY OF THE INVENTION

A transmitter for a magnetic body area network includes a power oscillator that directly uses a body coil as a resonant element. Shunt transistor circuitry is between the power oscillator and the body coil, the shunt transistor circuitry selectively shunts current from the body coil in response to a data signal provided to the transmitter. Power injection circuitry is synchronized to the power oscillator to selectively inject power into the body coil in response to the data signal. A tuning capacitor array is disposed to tune frequency in the body coil. A frequency-locked-loop responds to a frequency in the body coil and tunes the tuning capacitor array to lock to a carrier frequency. Very high Q coils can be used while achieving high data transmission rates of 5 mbps to 10 mbps. Transmitters and methods are applicable to on-off-key modulation, frequency-shift modulation and amplitude-shift modulation.

A method for transmitting via a body area includes generating a crystal referenced carrier signal. A data signal is received to be applied via the carrier signal to a body worn coil. Current is selectively shunted through transistors to from the body coil in response to a data signal. Current is selectively injected into the body coil through a circuit synchronized to the carrier signal in response to the data signal. The carrier signal is locked via a frequency lock loop.

DETAILED DESCRIPTION OF THE PREFERRED EMBODIMENTS

Figure 1:
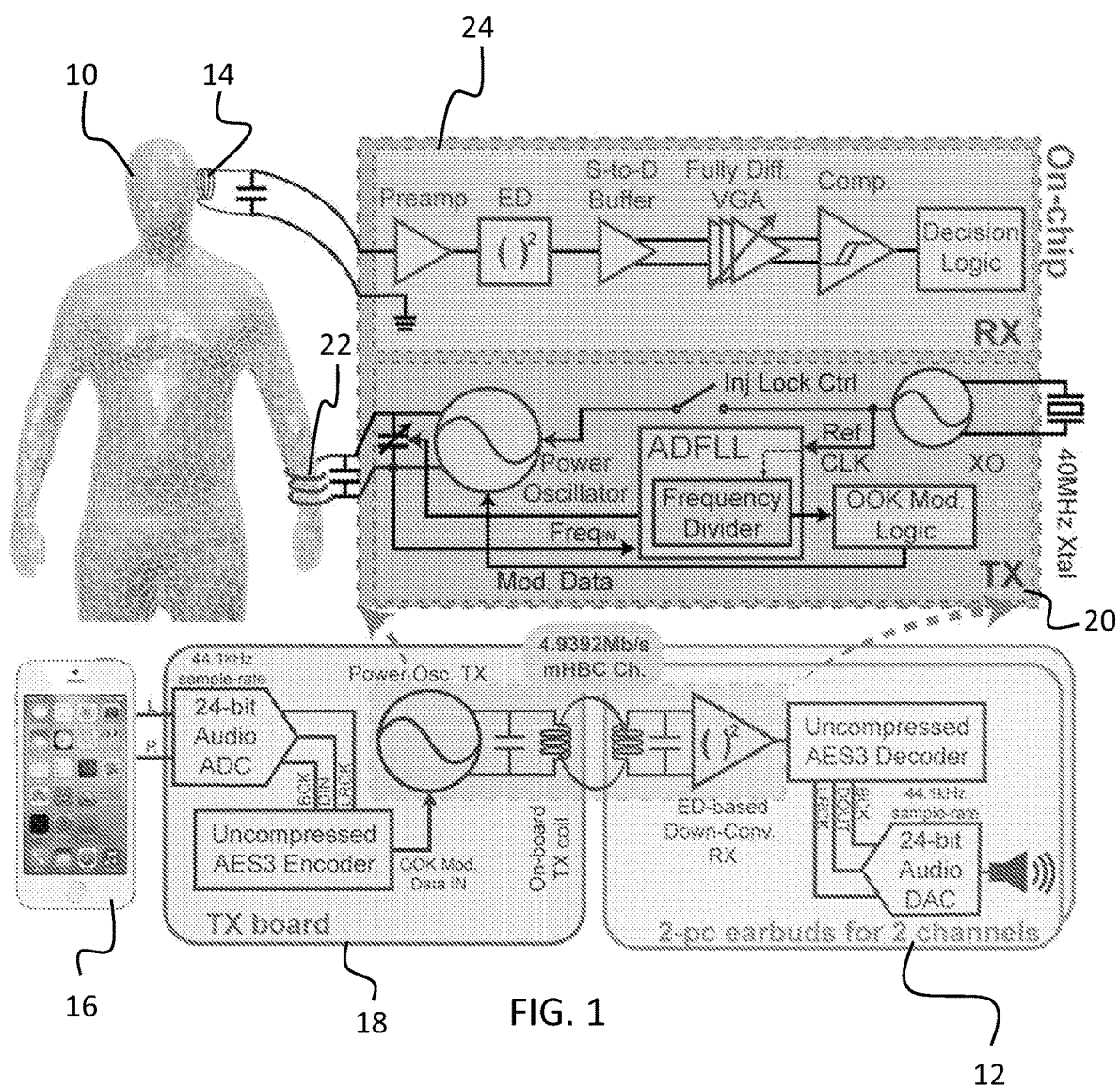
FIG. 1 illustrates preferred mHBC transceiver system of the invention with external devices that benefit from the mHBC transceiver system.

A mHBC transceiver (TRX) is provided that can efficiently exploit the magnetic HBC while reducing the limitations experienced with prior transmitters, which can limit data rate of a straightforward approach to <800 kb/s with a high-Q coil. A preferred transceiver and method can provide a high Q (ratio of the inductance L to the resistance R of a coil at a given frequency) transmission coil for low path loss, while maintaining bandwidth. Preferred high-Q coils have minimum Q of 10, preferably at least 10-20, more preferably 20-40, and can be 50 or more as demonstrated by experiments, and generally within the range of 10-100. Preferred methods and circuits include accelerated quenching and a kick-start circuit, and improve performance compared to previous known state-of-the art mHBC circuits.

In a preferred embodiment, an LC power oscillator drives a transmitter coil, which is beneficial due to its low power operation and low complexity for on-off-keying (OOK) data modulation as well as for resonance tuning. The present invention can also be use in frequency-shift keying (FSK) or amplitude-shift keying (ASK). Normally, high Q coils prevent fast voltage variation of an LC tank by storing the inductive energy as currents in coils. When that happens, Q clock cycles are required to convey the on-off signal variation, while limiting its data rate. Preferred embodiment transceiver circuits include a differential PMOS or NMOS switch pair parallelly connected with an LC resonator for fast off-period response by shorting two TX output nodes to VDD while a tail high-Vt switch (leakage current reduction transistor) prevents excess leakage currents in off-period. An injection locking amplifier provides for fast recovery of LC oscillation in on-periods. When the injection locking block provides enough gain for fast oscillation recovery, the LC tank enables fast (relative to the center frequency divided by the Q factor, e.g. 5 or 10 Mbps) bitrate OOK data transmission. As mentioned above, FSK and ASK are alternatives.

A body-worn coil has inevitable impedance variation due to its shape changing and/or its interface with a human body. This varying impedance (especially, reactance) can cause LC resonance to be out of tune; as a result, the path gain is degraded, and the injection locking can fail. Preferred methods and circuits address this issue via automatic resonance tuning with a frequency locked loop, preferably a digitally implemented frequency locked loop (FLL). By comparing the LC resonant frequency to the reference clock provided by a crystal oscillator, the FLL output bits can control the tuning capacitor array so that the LC resonance matches the reference clock. By implementing the compensation techniques for high Q TX coil, an RX coil can be optimized for low power operation with having the reasonable Q for data transferring bandwidth. Experiments demonstrated with RX coils whose Q is 8 for 5 MHz bandwidth with 40 MHz carrier frequency, and minimized the power consumption by employing a mixer-free downconverting OOK demodulation.

Preferred embodiment transmitters can provide high data rate transmission rates into an mHBC. An example embodiment consumes <40 μW at a data rate of 5 Mb/s, for the lowest energy/bit amongst pragmatic prior art wireless BANs. Efficient operation is achieved by: 1) exploiting the intrinsically low path loss between high-Q mHBC coils to reduce TX output power and RX gain/noise requirements; 2) employing an mHBC coil as a high-Q resonant element in an energy-efficient directly-OOK-modulated power oscillator (PO); 3) communicating at a high data rate (5 Mb/s) despite the high-Q TX coil, which nominally limits bandwidth to <800 kHz, via an all-digital frequency-locked-loop (AD-FLL)-based synchronous injection-locked accelerated quenching and kick-start circuit, which also serves to dynamically tune the TX resonant capacitor array to maintain center frequency lock between TX and RX while compensating the impedance variation of body-worn coils; and 4) biasing dynamic-threshold MOS (DTMOS) RX amplifiers and envelope detector (ED) in deep subthreshold, all at link-budget-appropriate noise levels.

A preferred transmitter for a magnetic body area network includes a power oscillator that directly uses a body coil as a resonant element. The transmitter has shunt transistor circuitry between the power oscillator and the body coil, the shunt transistor circuitry selectively shunting current from the body coil in response to a data signal provided to the transmitter. The transmitter includes power injection circuitry synchronized to the power oscillator to selectively inject power into the body coil in response to the data signal. A tuning capacitor array is disposed to tune frequency in the body coil. A frequency-locked-loop that responds to a frequency in the body coil and tunes the tuning capacitor array to lock to a carrier frequency. The frequency-locked-loop is preferably a digital circuit that compares resonance frequency of the body coil to a crystal-generated reference and produces an output to adjust tuning of the capacitor array to increase or decrease the resonance frequency in the tuning capacitor array. A low leakage transistor or switch can inhibit leakage current when power is not applied to the resonant element. The transmitter is preferably packaged and connected to the body coil, which is configured to be worn on a body of person, such as a forearm. The data signal can have data at rate of 5 Mbps to 10 MBps and the body coil can have a high Q factor of 10-100. The body coil is preferably a center tapped coil, and the shunt transistor circuitry and power injection circuitry are connected to opposite ends of the center tapped coil. A transmitter can consume <40 μW at a data rate of 5 Mb/s. The frequency-locked-loop can conduct frequency tuning within 10-20 μs between packets in the data signal.

The data signal can be a frequency-shift keying signal. The injection transistor circuitry is modulated to assist a move to a new frequency, and the shunting with the injection speeds response to change of frequency corresponding to the data signal.

The data signal can be an amplitude-shift keying signal. The shunting transistor circuitry is duty-cycle modulated, for a time to assist change to a lower amplitude corresponding to the data signal, and the power injection circuitry injects power to speed change a higher amplitude corresponding to the data signal.

The data signal can be an on-off-keying signal (OOK). The shunt transistor circuitry shunts current from the body coil in response to a first change in the data signal provided to the transmitter, and the power injection circuitry injects power into the body coil in response to a second change in the data signal that is opposite the first change in the data signal. The first change in the data signal can be a change from data "1" to data "0", and the second change in the data signal can be a change from data "0" to data "1".

A preferred magnetic body area network includes a transmitter as described and further includes a receiver. The receiver includes a preamplifier circuit connected to a magnetic receive coil to amplify the received data signals to a larger level, an envelope detector circuit to demodulate signals from the preamplifier to baseband, and additional amplification circuitry to amplify signals from the envelope detector and supply amplified signals to a comparator. The preamplifier circuit, envelope detector circuitry, and additional amplification circuitry preferably are constructed from biased dynamic-threshold MOS (DTMOS) transistors biased in deep subthreshold.

A preferred method for transmitting via a body area network includes generating a crystal referenced carrier signal; receiving a data signal to be applied via the carrier signal to a body worn coil; shunting current selectively through transistors to from the body coil in response to a data signal; injecting current selectively into the body coil through a circuit synchronized to the carrier signal in response to the data signal; and frequency locking the carrier signal via a frequency lock loop.

In a preferred method, the data signal is an on-off-keying signal, the shunting removes power from the body coil to speed removal of current from the body coil in response to a change from a data "1" to a data "0"; and the injecting injects current in response to a change from data "0" to a data "1".

In a preferred method, the data signal is a frequency-shift keying signal, the injecting current injects modulated current to assist a move to a new frequency, and the shunting speeds response to change of frequency corresponding to the data signal.

In a preferred method, the data signal is an amplitude-shift keying signal, the shunting includes duty-cycle modulation for a time to assist change to a lower amplitude corresponding to the data signal, and the injecting injects power to speed change a higher amplitude corresponding to the data signal.

Preferred embodiments of the invention will now be discussed with respect to the drawings and with respect to experiments. The drawings may include schematic representations, which will be understood by artisans in view of the general knowledge in the art and the description that follows. Features may be exaggerated in the drawings for emphasis, and features may not be to scale.

FIG. 1 illustrates a preferred mHBC transceiver system of the invention with devices that benefit from the mHBC transceiver system. A person 10 wears earbuds 12 that have an antenna coil 14. Earbuds 12 are an example audio DAC to drive a speaker, which receives bits from a receiver of the present system. A device 16 includes a transmitter board 18. The transmitter board 18 contains an mHBC transmitter 20 circuit, and standard components, such as audio ADC and an AES3 encoder. The mHBC transmitter circuit 20 leverages a coil 22 that is shown as being worn on a forearm, and could be, for example, part of clothing, a wrist band or another. The earbuds 12 include an on-chip mHBC receiving circuit 24.

Figure 2A:
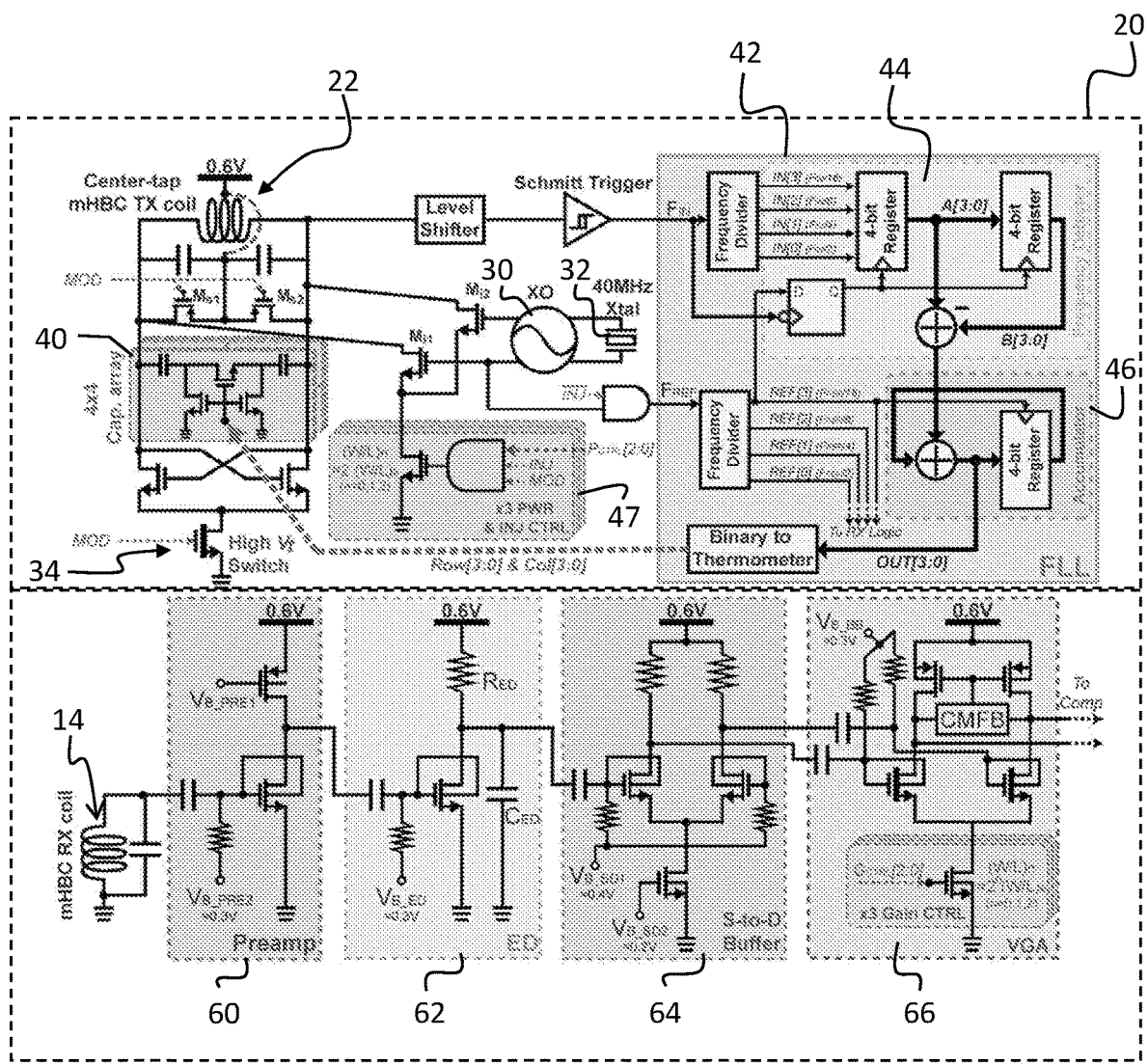
FIGS. 2A and 2B illustration preferred mHBC transmitter and receiver circuits.

With reference to FIG. 2A, the mHBC transmitter circuit 20 utilizes a power oscillator 30 having a crystal reference 32 to directly generate a 40 MHz carrier by directly using the mHBC coil 22 itself as the resonant element in the oscillator. The Q of the TX coil 22 can be large (e.g., 50). In such case, driving the power oscillator 30 on and off for OOK modulation via the tail current source transistor 34 cannot be normally accomplished at a data rate faster than 800 kb/s. This is one of the reasons why conventional near-field communication (NFC) protocols implementing low-frequency (<13.56 MHz) near-field coupling (as opposed to simultaneous near- and far-field coupling at a higher frequency in mHBC) cannot support sufficiently high data rates. In the present embodiment of FIG. 2A, to increase data rate, switching transistors $M_{s1}$ and $M_{s2}$ rapidly shunt the inductor (body coil 22) current during transmissions of logic '0's. To rapidly quench oscillations without having to wait for Q cycles, which serves to dynamically reduce the tank's Q-factor during off times while improving the quench rate by 10.5×. On the other hand, to rapidly kick-start oscillations when transmitting logic '1's, which would normally take more cycles at 40 MHz than are available in a 5 Mb/s symbol period, injection transistors $M_{i1}$ and $M_{i2}$ improve oscillation startup time by 20×. For ASK, the switch 34 is an array of High-Vt switches. The MOD signal is then a multi-bit digital signal that controls the array of High-Vt switches, which can be, for example a binary-weighted array of High-Vt switches. This then serves to vary the amplitude of the oscillation according to the input data signal. The multi-bit MOD signal, when applied to the shunting transistors $M_{s1}$ and $M_{s2}$ is duty-cycle modulated according to the ASK data signal to shunt current away for the appropriate amount of time before arriving at the correct new amplitude level. The 'kick-start' via injection transistors $M_{i1}$ and $M_{i2}$ is used to reach ASK levels that are higher than the current level, while the shorting transistors would be activated for the right amount of time (via a duty-cycle modulation) to short the coil out until it reaches the desired. For FSK the Row[3:0] and Col[3:0] signals sent from the ADFLL 46 are modulated to adjust the center frequency of the transmitter. Injection switches in $M_{s1}$ and $M_{s2}$ inject current to more rapidly bring the new frequency to settle. The shunting and injection at a new frequency can help improve the speed of FSK modulation.

To maximize the effect of injection-locked kick-start, the resonant frequency of the power oscillator, which can change slightly with posture or environmental variation (though not as severely as in eHBC), is precisely set to the same frequency as the crystal-based injection source (30 and 32) for synchronous injection via a unit-capacitor array 40, e.g., 4×4, that is dynamically tuned via an all digital frequency lock loop ADFLL 42. This also helps to minimize any frequency mismatching between TX and RX. The fast control bit output (2.5 Moutput/s) of the ADFLL enables frequency tuning within 10-20 μs, and is only activated between packets every 1-10 ms, which is sufficient to compensate for slow inductance changes (>50-ms scale) of wearable coils. The ADFLL 42 includes a frequency detector 44 and an accumulator 46. During operation, the ADFLL 42 senses the oscillation frequency of the mHBC transmission through the coil 22 and compares it to that of the crystal reference from the crystal-based injection source 30 and 32. When the ADFLL 42 senses a difference, will digitally increment (or decrement) the capacitor array 44 until the frequencies are matched. Power and injection control 47 injects energy In phase with the turn-on sequence to improve the start-up time of the oscillator and increase the oscillation amplitude. Thus, the crystal-based injection source 30 and 32 uses the power an injection control 47 and transistors $M_{i1}$ and $M_{i2}$ to perform injection. The rapid kick-start and quenching circuits, along with the ADFLL 42, help to decouple the bandwidth-path loss trade-off The transmitter 20 successfully generates OOK modulated outputs at 5 Mbps even with a Q of 50 for good path loss. While an ADFLL is preferred for low power and ease of integrations, other types of frequency (phase) lock loops can also provide the comparison and incremental locking to the desired transmission frequency.

Figure 2B:
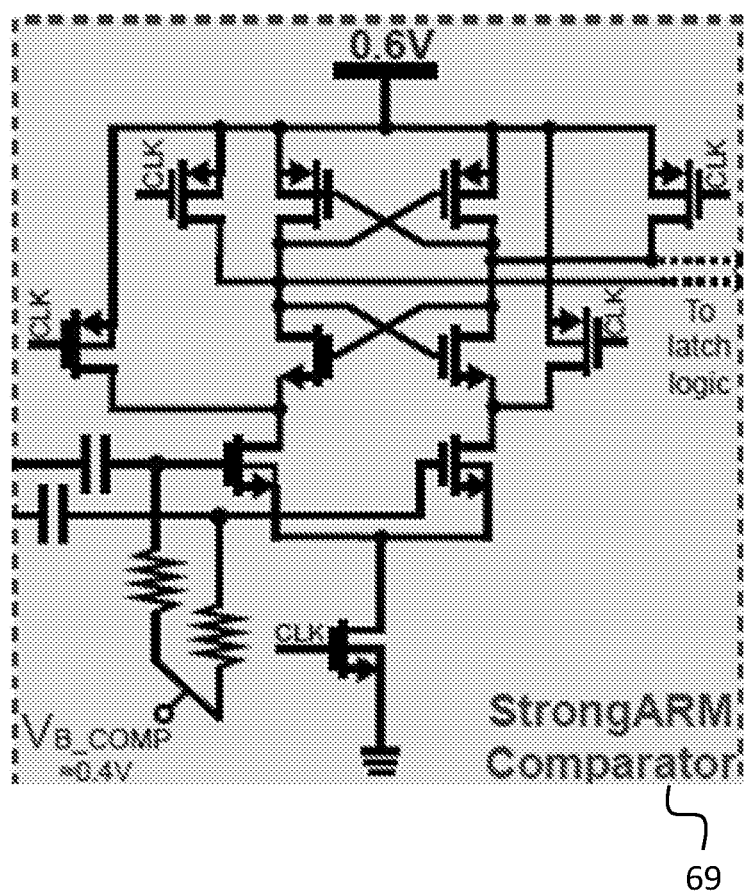

The mHBC receiver 24, shown in FIG. 2A with a preferred comparator in FIG. 2B, is designed using a common-source (CS) preamplifier 60, an active CS envelope detector (ED) 62, a single-ended-to-differential (S-to-D) buffer 64, and variable gain amplifier (VGA) 66. The preamplifier 60 amplifies the received signal to large levels. The ED 62 demodulates the signals to baseband. The S-to-D buffer and VGA further amplify the signal. All of these RX circuits are biased in subthreshold and utilize dynamic threshold transistor (DTMOS) inputs to improve transconductance or conversion gain by up to 32% iso-current. The ED 62 output drives the S-to-D buffer 64 designed with low-Vt devices to minimize input capacitance to help ensure 2.5 MHz bandwidth at the output of the low-current ED; the S-to-D buffer 64 then drives the differential VGA 66. The VGA output is bit-sliced via a regenerative comparator at the appropriate common-mode voltage thanks to the VGA's common-mode feedback (CMFB) circuit.

Because the ED 62 performs down-conversion utilizing 2nd-order intermodulation harmonics, the conversion gain, $A_{v,conv}$, is determined by the 2nd-order transconductance, $g_{m2}$, of the employed MOSFET, and the magnitude of the input fundamental carrier tone. Without proper filtering, all broadband interference will be down-converted to baseband, which causes demodulation failure. To minimize this issue, high-Q front-end filters can be used to reject interference. However, the system of FIG. 2 alleviates this need. The mHBC receiver 24 inherently provides a bandpass filter via its RX coil 14. There is no simple method to enable wideband data reception at the RX without a priori knowledge of the incoming data, but a low-Q coil is used (the same coil as the TX could be used, but with intentionally de-Q-ing resistors added to the tank). Despite a lower than normally desired Q (e.g., QRX=8 here for 5-Mbps data transfer), the coil 14 demonstrates rejection of interference at the 2.4 GHz ISM band, the FM radio band, and the 13.56 MHz NFC ISM band by up to 56 dB, 33 dB, and 22 dB, respectively. More importantly, the body itself helps to provide additional rejection. RF radios and other off-body magnetic sources (e.g., NFC) have up to 80 dB and 25 dB more path loss around the body than on-body mHBC, respectively. Therefore, a direct-ED architecture, when used in an mHBC receiver, can tolerate reasonable levels of out-of-band interference, and can thus enable a low-power implementation. Lab testing of a receiver according to FIG. 2 in a typical unshielded lab environment did not show any interference sensitivities. The preamp 60 improves conversion gain, $A_{v,conv}$, and increases RX sensitivity.

After envelope detection, the single-to-differential (S-to-D) buffer 64 is used to lessen susceptibility to power supply fluctuations and provide low-pass filtering that helps to reject high-frequency harmonics. Preferably, the S-to-D buffer 64 includes low-Vt devices to minimize input capacitance, which helped an experimental receiver in ensure a 2.5 MHz cut-off frequency of the ED RC filter ($R_{ED}$=400 kΩ, and $C_{ED}$=150 fF). The S-to-D buffer 64 then drives the fully-differential variable gain amplifier (VGA) 66. While the VGA 66 compensates the variable noise level of an ultra-low power comparator 69 (FIG. 2B), the VGA 66 includes a common-mode feedback (CMFB) circuit that adjusts the common-mode voltage of VGA output to the appropriate value to minimize the error of the next-stage comparator 69. Also, by implementing the oversampling decision scheme the ultra-low power StrongARM comparator 69 and following conventional latch logic (not shown), the RX architecture can successfully demodulate data without a power-hungry synchronization block. For the better impedance matching performance between the mHBC RX coil and the RX input, the experimental RX coil was designed for the parallel resistance (RP) at the resonant frequency (40 MHz) of the LC tank to have the same resistance value of the RX input.

Figure 3:
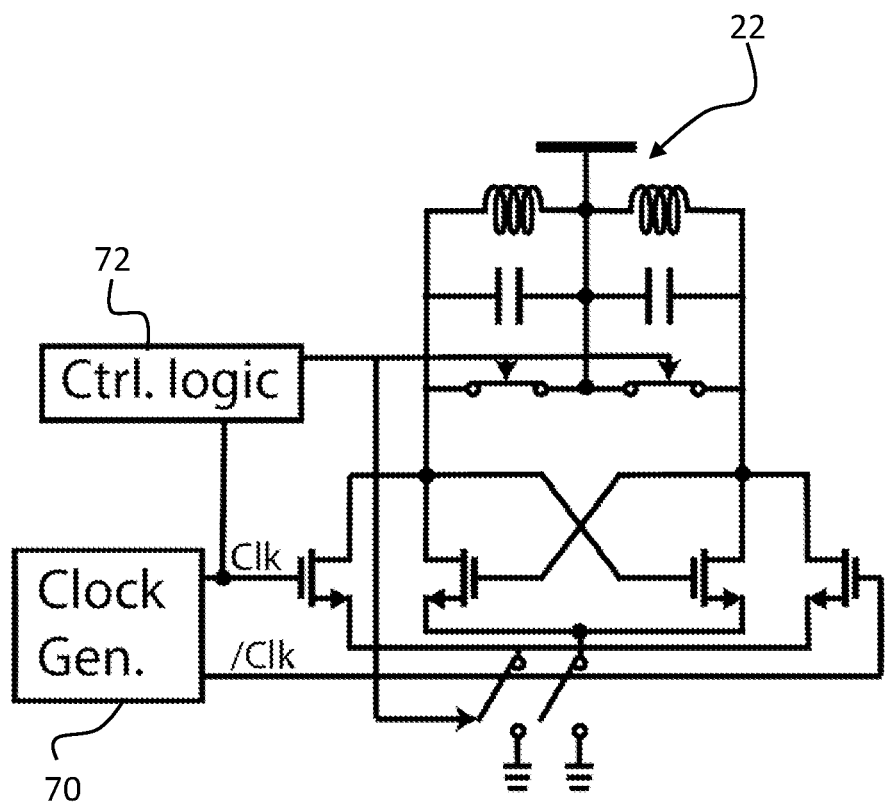
FIG. 3 is a functional representation of injection locking performed by the FIG. 2A mHBC transmitter circuit.

FIG. 3 is a functional representation of the injection locking of the mHBC transmitter 20. Clock generation 70 represents the the crystal-based injection source 30 and 32 uses the power and injection control 47 and transistors $M_{i1}$ and $M_{i2}$ to perform injection. The control logic 72 is representative of the kick-start provided by injection transistors $M_{i1}$ and $M_{i2}$ when transitioning from to a "1" from a "0". The clock generation 70 and control logic 72 perform injection locking to help the oscillation recover quickly after a turning-off period. In a preferred embodiment, the injection locking turns on after 5 μs and turns off during an off-period.

Figure 4:
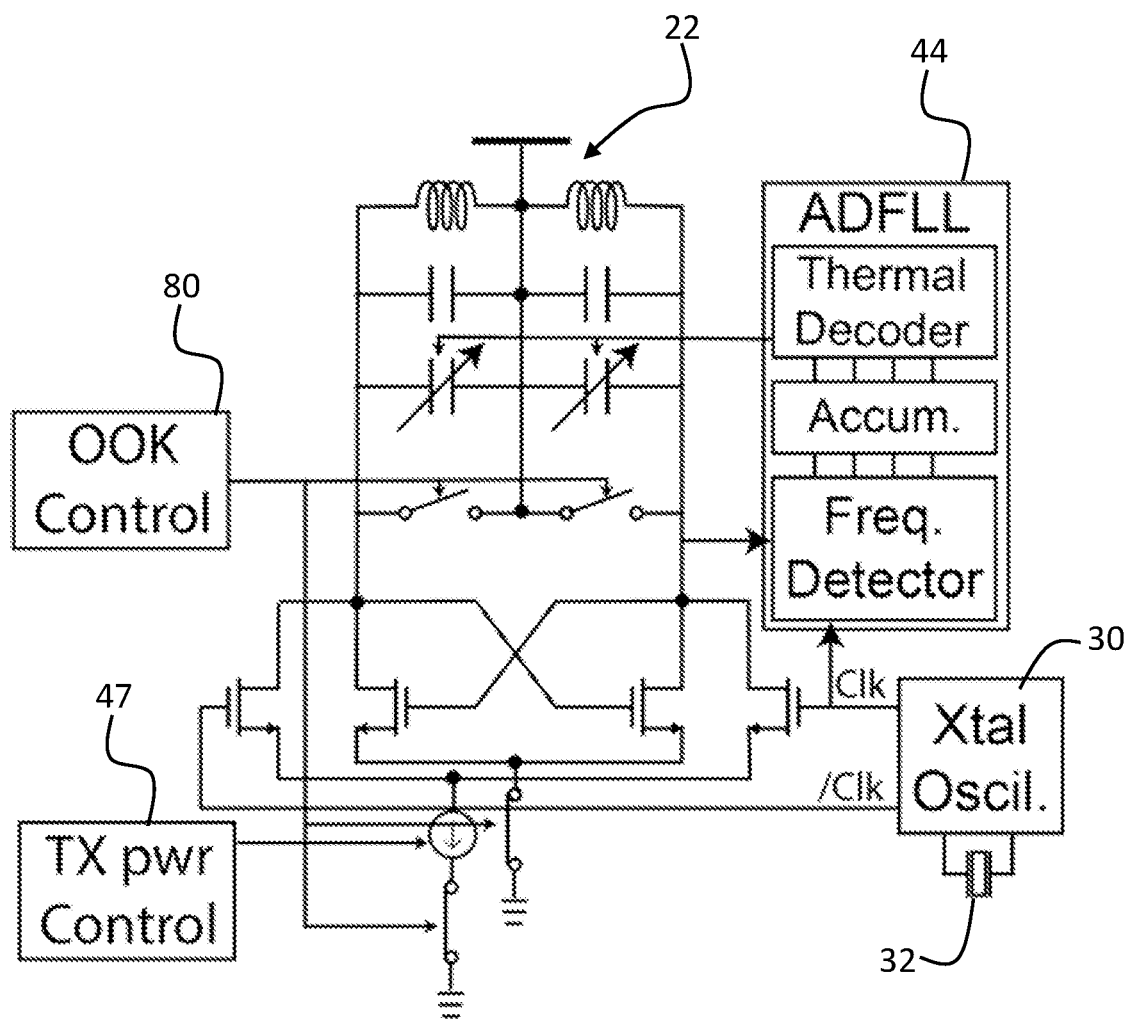
FIG. 4 is functional representation of the tuning of the resonance conducted in the mHBc transmitter of FIG. 2A while an OOK(on-off-keying) transmitter data signal is applied.

FIG. 4 is functional representation of the tuning of the resonance conducted in the mHBc transmitted 24 while OOK transmitter control 80 is conducted. The ADFLL automatically tunes the resonance of the carrier frequency (in the example is 40 MHZ) by controlling the tuning capacitance.

An experimental prototype in accordance with FIGS. 1-4 was fabricated in 0.12 mm² of core area in 65 nm CMOS.

Figure 5A:
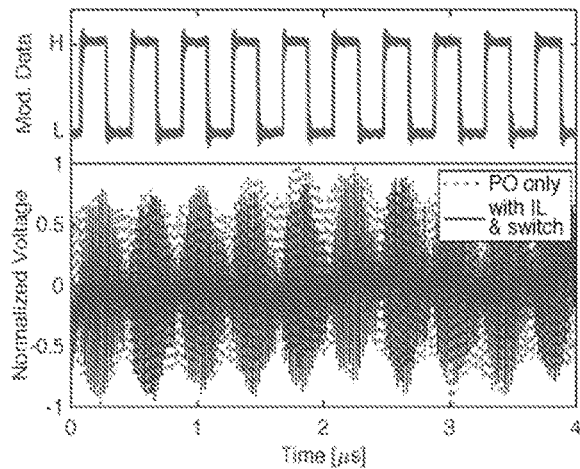
FIGS. 5A-5D illustrate performance of an experimental transceiver system in accordance with FIGS. 1-4.
Figure 5B:
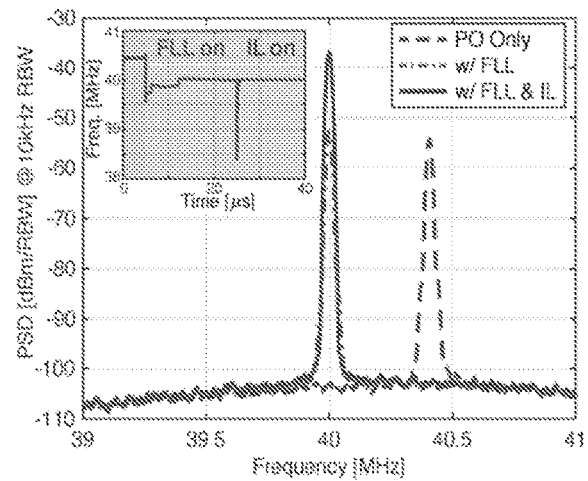
Figure 5C:
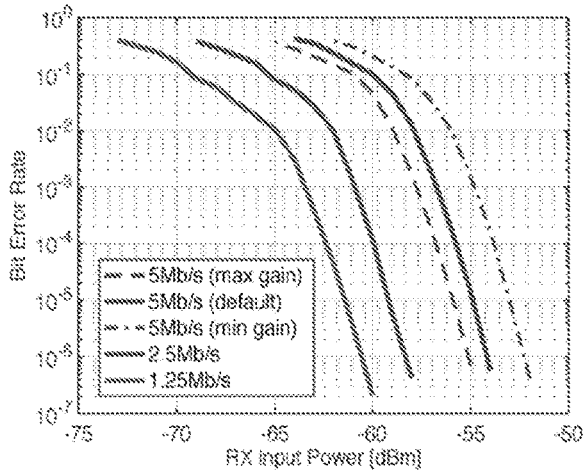
Figure 5D:
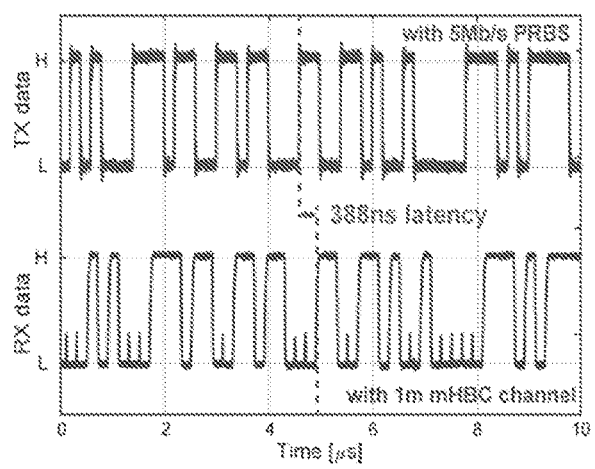

FIG. 5A shows the output waveform of the TX under worst-case modulation of alternating 1s and 0s at 5 Mb/s. Thanks to the accelerated quenching and kick-start circuit, the ASK-like modulation index improves from 15.4% to 84.7% compared to a conventional power oscillator, thereby enabling the desired high data rate in a manner that is compatible with the low-complexity RX. The spectrum of a signal received by an mHBC coil across a 10 cm channel is shown in FIG. 5B. Here, it can be seen that the ADFLL automatically re-tunes the intentionally-mis-tuned PO resonance frequency (~40.4 MHz) of TX to the correct carrier frequency (40 MHz), while also demonstrating that injection locking further improves total TX output power by 17.4 dB while providing the rapid kick-start behavior described above. The inset plot illustrates the frequency-tracking capability of the TX, while validating the fast frequency settling (<10 μs) of the ADFLL. BER testing in FIG. 5C under asynchronous operating conditions with 2× oversampling demonstrates receiver sensitivities of −63.5 dBm to −56 dBm at data rates from 1.25-to-5 Mb/s, respectively, and from −57 dBm to −54 dBm according to VGA gain setting at 5 Mb/s. When operating over a distance of ~1 m across a human body, a pair of mHBC TRXs, with −24.8 dBm TX output power and the −56 dBm RX sensitivity setting, achieved a TX-to-RX latency at 5 Mb/s of 388 ns with error-free operation, as shown in FIG. 5D.

To demonstrate feasibility of a practical application, two-channel analog audio data was generated by a smartphone and delivered via a two-channel 24b ADC and AES3 encoder to an mHBC TX employing a 2-turn 1-mm width coil printed on the outline of 11×5.5 cm² 1-oz copper PCB mounted on the smartphone. An mHBC RX, employing a 32 mm-diameter coil mounted within an in-ear headphone prototype, wirelessly received data, playing audio data through a speaker via an AES3 decoder and DAC. The test set up is represented by FIG. 1. Audio was delivered from the smartphone case to the headphone prototype across the body with no bit errors and <90 μs latency (dominated by the 88 μs of latency of the AES3 decoder).

The experimental TX consumes 18.6 μW at −24.8 dBm of output power, resulting in an efficiency of 3.7 pJ/bit at 5 Mb/s. At −56 dBm sensitivity, the RX consumes 6.3 μW for an efficiency of 1.3 pJ/bit. When including the power of a 17.2 μW crystal oscillator, the TX and RX consume 35.8 μW (7.2 pJ/bit) and 23.5 μW (4.7 pJ/bit), respectively, all while reliably covering a ~1.5 m BAN. This is the lowest power and most efficient TRX amongst prior-art that reliably communicate over a BAN and that includes the power consumption of frequency synthesis.

While specific embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the appended claims.

The invention claimed is:

1. A transmitter for a magnetic body area network comprising:
   a power oscillator that directly uses a body coil as a resonant element;
   shunt transistor circuitry between the power oscillator and the body coil, the shunt transistor circuitry selectively shunting current from the body coil in response to a data signal provided to the transmitter;

power injection circuitry synchronized to the power oscillator to selectively inject power into the body coil in response to the data signal;
a tuning capacitor array disposed to tune frequency in the body coil; and
a frequency-locked-loop that responds to a frequency in the body coil and tunes the tuning capacitor array to lock to a carrier frequency.

2. The transmitter of claim 1, wherein the data signal is a frequency-shift keying signal, the injection transistor circuitry is modulated to assist a move to a new frequency, and the shunting with the injection speeds response to change of frequency corresponding to the data signal.

3. The transmitter of claim 1, wherein the data signal is an amplitude-shift keying signal, the shunting transistor circuitry is duty-cycle modulated for a time to assist change to a lower amplitude corresponding to the data signal, and the power injection circuitry injects power to speed change a higher amplitude corresponding to the data signal.

4. The transmitter of claim 1, wherein the data signal is an on-off-keying signal (OOK), the shunt transistor circuitry shunts current from the body coil in response to a first change in the data signal provided to the transmitter, and the power injection circuitry injects power into the body coil in response to a second change in the data signal that is opposite the first change in the data signal.

5. The transmitter of claim 4, wherein the first change in the data signal comprises a change from data "1" to data "0", and the second change in the data signal comprises a change from data "0" to data "1".

6. The transmitter of claim 1, wherein the frequency-locked-loop comprises a digital circuit that compares resonance frequency of the body coil to a crystal-generated reference and produces an output to adjust tuning of the capacitor array to increase or decrease the resonance frequency in the tuning capacitor array.

7. The transmitter of claim 1, comprising a low leakage transistor or switch to inhibit leakage current when power is not applied to the resonant element.

8. The transmitter of claim 1, packaged and connected to the body coil, which is configured to be worn on a body of person.

9. The transmitter of claim 1, wherein the data signal provides data at a rate of 5 Mbps to 10 MBps and the body coil has a high Q factor of 10-100.

10. The transmitter of claim 1, wherein the body coil is a center tapped coil, and the shunt transistor circuitry and power injection circuitry are connected to opposite ends of the center tapped coil.

11. The transmitter of claim 1, consuming <40 μW at a data rate of 5 Mb/s.

12. The transmitter of claim 1, wherein the frequency-locked-loop conducts frequency tuning within 10-20 μs between packets in the data signal.

13. A magnetic body area network comprising a transmitter of claim 1 and a receiver, the receiver comprising:
a preamplifier circuit connected to a magnetic receive coil to amplify the received data signals to a larger level;
an envelope detector circuit to demodulate signals from the preamplifier to baseband; and
additional amplification circuitry to amplify signals from the envelope detector and supply amplified signals to a comparator.

14. The network of claim 13, wherein the preamplifier circuit, envelope detector circuitry, and additional amplification circuitry comprise biased dynamic-threshold MOS (DTMOS) transistors biased in deep subthreshold.

15. A method for transmitting via a body area network the method comprising:
generating a crystal referenced carrier signal;
receiving a data signal to be applied via the carrier signal to a body worn coil;
oscillating a magnetic human body communication power oscillator referenced to the crystal referenced carrier signal connected across the body worn coil through current injection transistors to use the body worn coil as a resonant element;
dynamically tuning a unit-capacitor array to a frequency locked loop, wherein the unit-capacitor array is connected across the body worn coil, wherein the power oscillator is set for synchronous injection to the body worn coil to minimize frequency mismatching between transmission and reception, wherein the frequency locked loop senses a transmission frequency, compares it to the crystal referenced carrier signal, and digitally increments or decrements the unit-capacitor to match the transmission frequency and the crystal referenced carrier signal;
controlling an array of high-Vt switches connected to the unit-capacitor array via a multi-bit data modulation signal; and
controlling the current injection transistors via an injection control circuit that is duty-cycle modulated in accordance with the multi-bit data modulation signal.

16. The method of claim 15, wherein the multi-bit data modulation signal is an on-off-keying signal, the method comprising
shunting through shunting transistors connected to shunt power from the body worn coil to remove power from the body coil to speed removal of current from the body worn coil in response to a change from a data "1" to a data "0";
injecting current through the current injection transistors in response to a change from data "0" to a data "1".

17. The method of claim 15, wherein the multi-bit data modulation signal is a frequency-shift keying signal, the method comprising injecting current comprises injecting modulated current through the current injection transistors to assist a move to a new frequency, and comprising shunting through shunting transistors connected to shunt power from the body worn coil to remove power from the body coil in response to change of frequency corresponding to the multi-bit data modulation signal.

18. The method of claim 15, wherein the multi-bit data modulation signal is an amplitude-shift keying signal, can comprising shunting through shunting transistors connected to shunt power from the body worn coil to remove power from the body coil in to assist change to a lower amplitude corresponding to the multi-bit data modulation signal, and injecting current through the current injection transistors to speed change a higher amplitude corresponding to the multi-bit data modulation signal.

* * * * *